Figure 1:
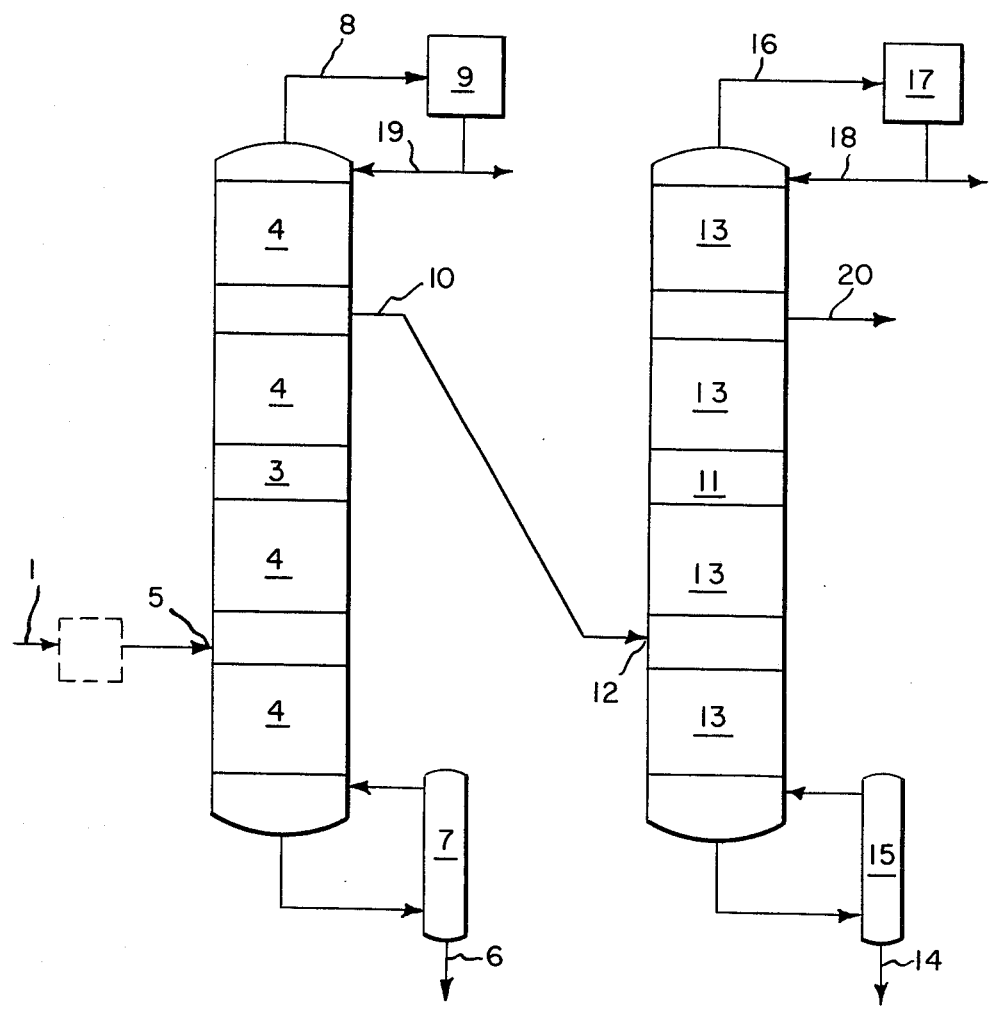

United States Patent [19]

Ernst et al.

[11] 4,383,895
[45] May 17, 1983

[54] PURIFICATION OF 1,4-BUTANEDIOL

[75] Inventors: Richard E. Ernst, Kennett Square, Pa.; Donald C. Paul, Wilmington, Del.

[73] Assignee: E. I. Du Pont de Nemours and Company, Wilmington, Del.

[21] Appl. No.: 304,106

[22] Filed: Sep. 21, 1981

Related U.S. Application Data

[63] Continuation-in-part of Ser. No. 179,948, Aug. 21, 1980, abandoned.

[51] Int. Cl.³ .............................................. B01D 3/10
[52] U.S. Cl. ........................................ 203/77; 203/91; 568/868
[58] Field of Search ................... 568/868; 203/77, 12, 203/14, 18, 91, 73, 80

[56] References Cited

U.S. PATENT DOCUMENTS

| | | | |
|---|---|---|---|
| 2,629,686 | 2/1953 | Grosser | 202/52 |
| 2,768,214 | 10/1956 | McKinley et al. | 260/637 |
| 2,950,326 | 8/1960 | Hort | 260/635 |
| 2,967,893 | 1/1961 | Hort et al. | 260/635 |
| 3,852,164 | 12/1974 | Chow et al. | 260/637 R |
| 3,891,511 | 6/1975 | Danneil et al. | 260/637 R |

FOREIGN PATENT DOCUMENTS

| | | |
|---|---|---|
| 529118 | 8/1956 | Canada . |
| 1025852 | 3/1958 | Fed. Rep. of Germany . |
| 973613 | 3/1960 | Fed. Rep. of Germany . |

*Primary Examiner*—Frank Sever

[57] ABSTRACT

Color-forming materials or their precursors present in crude 1,4-butanediol are reduced more efficiently by subjecting the crude 1,4-butanediol to distillation under conditions wherein substantially all the water present in the crude 1,4-butanediol is first removed and then the 1,4-butanediol with reduced water content is further distilled to remove the color-forming materials.

2 Claims, 2 Drawing Figures

PURIFICATION OF 1,4-BUTANEDIOL

CROSS-REFERENCE TO RELATED APPLICATION

This application is a continuation-in-part of copending application Ser. No. 179,948, filed Aug. 21, 1980, now abandoned.

DESCRIPTION

1. Technical Field

The process of the invention relates to a method for removing color-forming materials from crude 1,4-butanediol by distillation. More specifically, the process of the invention relates to a process for removing certain color-forming materials from crude 1,4-butanediol by first removing substantially all of the water present in the crude 1,4-butanediol and then removing the color formers.

2. Background Art 1,4-Butanediol, hereinafter referred to as BAD, is conventionally prepared by the catalytic hydrogenation of butynediol. The crude BAD from the hydrogenation contains water and among other impurities certain color-forming materials that are apparent when the BAD is subjected to the color test referred to hereinafter as the polyester color test.

The art teaches several methods for removing impurities and/or color formers from BAD, e.g., U.S. Pat. Nos. 2,629,686; 2,768,214; 3,852,164 and 3,389,511. However, the above methods either do not remove enough of color-forming materials present to provide the desired product or involve complicated and expensive routes for their removal.

DISCLOSURE OF THE INVENTION

Now it has been found that color-forming materials, or their precursors, present in crude BAD can be reduced more efficiently by subjecting the crude BAD to distillation under conditions wherein substantially all of the water present in the crude BAD is first removed and then the BAD with reduced water content is further distilled to sufficiently remove the color-forming materials to provide a product for use in the preparation of polyesters.

Crude BAD contains 1–20% by weight water and organic impurities that boil lower than BAD, 0.05–5% by weight of high boiling organic tars and inorganic salts, and 80–99% BAD. Among the organic impurities are various undesirable color formers including those that are apparent when the BAD is mixed with acids such as hydrochloric acid.

In a two-column embodiment of the process of the invention crude BAD is fed at the midpoint or lower but not below the packing or trays of a distillation column. If the column is filled with packing, many conventional types of packing can be employed, e.g., Koch Sulzer type mesh packing or stainless steel Pall rings. In some embodiments it may be desirable to use actual trays or a mixture of trays and packing. In a preferred embodiment the upper part of the column will be packing while the lower part will be trays with the feed of crude BAD being introduced into the tray portion. In most embodiments it will be preferable to have three or more theoretical trays in the column below the feed.

High boiling organic tars and inorganic salts are removed from the bottom of the distillation column or from a reboiler as a liquid purge. Low boiling organic impurities and water are removed from the top of the distillation column, condensed and a portion fed back as reflux while the rest is purged. The amount of reflux is not critical and can vary from a ratio of 1:1 to 5:1. At a point on the distillation column above the point where the feed is introduced into the column and below the top of the packing or trays in the distillation column, a liquid stream is removed that comprises BAD with substantially reduced water content relative to the feed, i.e., by substantially reduced is meant less than 5000 ppm, preferably less than 1500 ppm. The liquid stream should be removed two or more theoretical trays below the top of the column.

The operation of the column can be adjusted using conventional techniques to obtain this water content. The column is preferably operated under vacuum so that the temperature of distillation does not exceed 175° C., i.e., the maximum base temperature. At temperatures above 175° C. BAD tends to decompose into tetrahydrofuran and water. Thus, the column is usually operated under 200 mm Hg and preferably 60–100 mm Hg at the top and 120 mm Hg at the bottom.

The BAD stream with the reduced water content and still containing undesirable quantities of color formers is then fed into a second distillation column at the midpoint or lower but not below the packing, i.e., at least two theoretical trays above the bottom. High boiling organic tars are removed from the bottom or the reboiler, and low boiling organic impurities and most of the remaining water are removed from the top of the column, condensed and part refluxed to the column. At a point on the second distillation column above the feed and below the top of the packing, i.e., at least two theoretical trays below the top, a liquid stream is removed that comprises BAD substantially free from water and color-forming materials.

The color formers removed by the process of the invention are compounds that color the polyester product from the reaction of BAD and an appropriate dibasic acid. They are measured by first preparing a polyester with BAD and then following the test procedure described as ASTM D 1209 to measure the color. It has been found that impurities in the dibasic acid also contribute to the polyester color in relation to a given lot of dibasic acid. There is a relative reduction of color in the polyester product when the color formers are removed from BAD by the process of the invention. After second-stage distillation in the essential absence of water according to the present process, the BAD product is substantially free from these color formers.

The removal of the BAD stream from the first distillation column at a point above the midpoint, i.e., above the feed, but below the packing top level is important. Any removals above the packing will be in the form of vapors containing much larger amounts of water and will retard the removal of the color formers in the second-stage distillation. As the point of removal of the BAD stream approaches the point at which the crude BAD is fed, the amount of water present in the BAD stream increases. However, as long as the stream is removed above the feed level, its water content will be substantially reduced. The stream removed from the distillation column with reduced water content and sent to the second distillation column normally will be water white in appearance.

The range for withdrawing liquid BAD from the first distillation column is where the water content is from 0–5000 ppm, preferably below 2000 ppm and most preferred below 1500 ppm, irregardless of the water concentration in the crude BAD. It was found that the relative volatility of color formers out of BAD goes from 0.63 to 1.0 as the water is increased to 5000 ppm. Thus, the relatively volatility indicates the substantially more ready removal of color formers out of BAD at 0.63 as compared to 1.0.

In the second distillation column, the removal of the product stream below the top of the packing, i.e., at least two theoretical trays from the top, but above the feed level is also important. Removal at a level above the packing would mean removal of a vapor stream which would contain substantially more water.

The feed point to the second distillation column from the first column is not critical. It is only important that the feed be such that at least half of the packing is above the feed so that the removal of color formers is maximized. As previously mentioned, a stream of high boiling tars is removed from the bottom or reboiler of the second distillation column and a stream of low boiling organic impurities and water is removed from the top. The operating conditions in the second column can be substantially the same as in the first, i.e., operated under vacuum of at least 200 mm Hg and temperatures between 100°–175° C.

As set forth previously, the packing or trays used can be any of several commercially available. The packing can be confined in sections separated by perforated metal plates or screens. Any number of the sections can be in a distillation column.

FIG. 1 is a flow drawing illustrating an embodiment within the scope of the process of the invention. Referring now to the drawing crude BAD 1, optionally preheated in heater 2 is fed into distillation column 3 containing four sections of packing 4 of stainless steel Pall rings at a point 5 above the bottom packed section 4. High boiling organic tars 6 are removed from the bottom of the column through reboiler 7 and low boiling organic impurities 8 are removed from the top of the column, condensed 9, and part refluxed 19 to the column. A liquid stream 10 is removed below the top packed section of the column and sent to a second distillation column 11 at a point 12 above the bottom packed section 13 of the four sections in the column. High boiling organic tars 14 are removed from the bottom of the column through reboiler 15 and low boiling organic impurities 16 are removed from the top of the column, condensed 17, and part refluxed 18. A product stream 20 is removed below the top packed section with reduced water and color formers.

The process of the present invention permits the efficient removal of the color former by first reducing the water content of the crude BAD. This process has been illustrated by the use of two distillation columns. It is, of course, possible to use more than two columns as long as they are operated to remove the water first.

Figure 2:
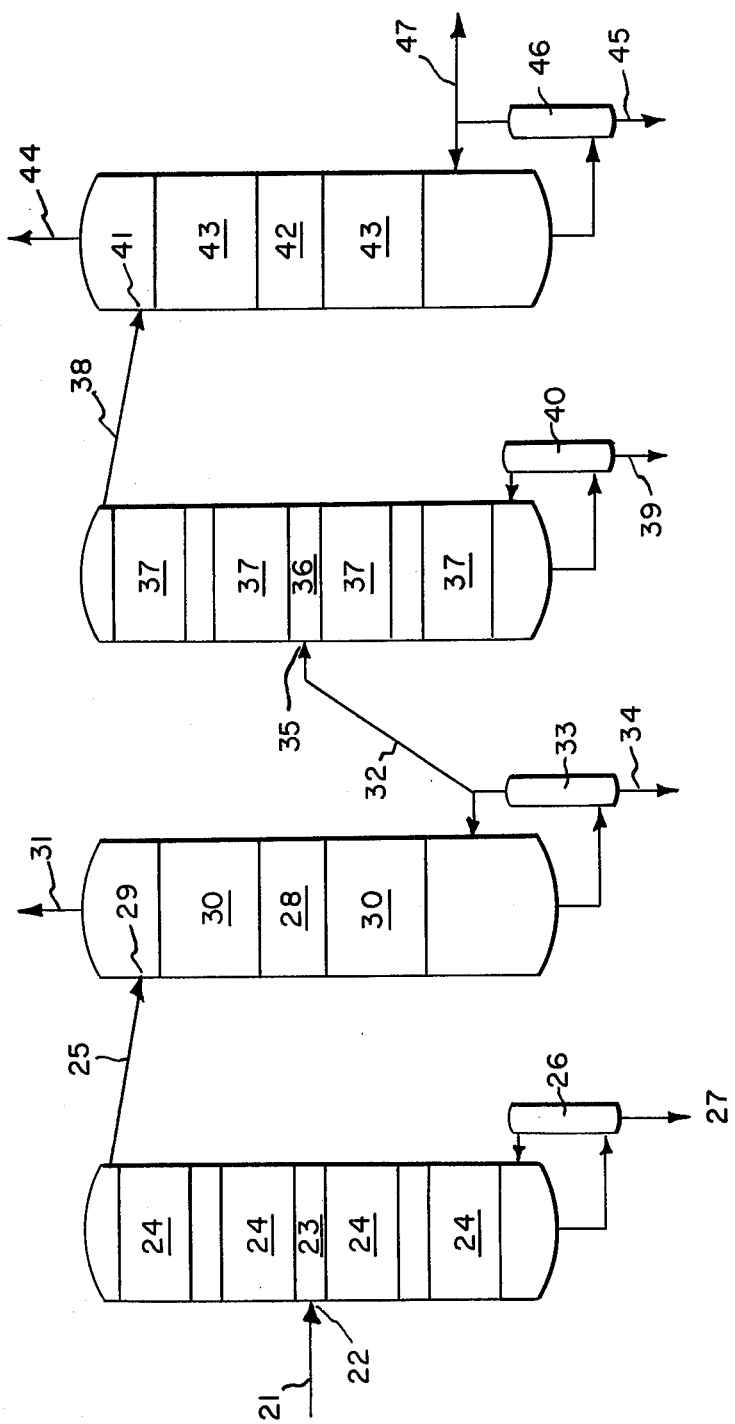

FIG. 2 teaches a four-column embodiment of the process of the invention. In this process crude BAD 21 is fed to the middle 22 of the first distillation column 23 containing four packed sections 24. A liquid product draw is removed at the top of the column 25. A high boiler purge 27 is removed from the reboiler 26.

The overhead product 25 is fed into a second distillation column 28 containing two packed sections 30 at point 29 above the second packed section. Water and light boilers are removed from the top of the column 31. The relatively dry product 32 ($H_2O$ less than 400 ppm) is removed as a vapor draw from the reboiler 33 and high boilers are purged 34.

The dry vapor 32 is fed into the middle 35 of a third distillation column 36 containing four packed sections 37. A liquid overhead product 38 low in high boilers is removed with a liquid bottom purge 39 from the reboiler 40.

The overhead product 38 is fed into the top 41 of a fourth column 42 which contains two packed sections 43. A vapor purge 44 is removed from the top and a liquid purge 45 is removed from the reboiler 46. The final product 47 is removed as a vapor from the reboiler 48. This material will be low in water content and produce a low polyester color. All four columns should be operated at a vacuum low enough, e.g., below 200 mm Hg, to maintain reboiler temperatures below 175° C.

The invention is further illustrated by the following example wherein all percentages or parts are by weight unless otherwise indicated.

The relative volatility of the color former out of BAD was determined in the absence and in the presence of water as follows:

EXAMPLE A (Absence of Water)

A sample of BAD (with <500 ppm water) was distilled to equilibrium in an Othmer still (which gives one theoretical plate of separation) at 160° C. at 75 mm Hg. Polyesters were prepared with adipic acid and the feed BAD, the overheads, and the pot, giving the following APHA color values:
 Feed: 70
 Overhead: 45
 Pot: 80

From this the relative volatility of the color former out of BAD was calculated to be 0.63.

EXAMPLE B (Presence of Water)

The same experiment described in A was repeated, except 1% water was added to the BAD before distillation. In this case the polyester prepared with adipic acid had the following APHA color values:
 Feed: 70
 Overhead: 80
 Pot: 80

From this it is seen that little or no separation of the color former from BAD is achieved by distillation in the presence of 1% water.

EXAMPLE C

Crude butanediol, containing 5% water, was fed to the 5th tray of a 13 tray, 1-inch diameter, Oldershaw column at 5 ml/min. The column pressure was maintained at 74 mm Hg. An overhead draw was taken at 1 ml/min with a 3:1 reflux ratio and a bottom purge was taken from the pot at 0.5 ml/min. The liquid product was drawn off of the 10th tray at 3.5 ml/min with a reflux ratio of 0.5:1. This product had 1400 ppm water and gave a polyester when reacted with adipic acid with an APHA color of 70. This intermediate product was then fed back through the same column at the same conditions giving a final product with 225 ppm water and a polyester with APHA color of 30.

Polyester Test Method 90 g of 1,4-butanediol and 104 g of adipic acid are charged to a 3 necked 500 ml RB flask equipped with a thermometer, distillation head, magnetic stirrer and a heating mantle. The system is evacuated and filled with N₂ three times and left under a slow N₂ flush. The flask is heated to 180° C. (N₂ flush is turned off when temperature reaches 140° C.), and is maintained at 180° C. for 7 hours. The resulting polyester is cooled to about 100° C. and the APHA color is measured by comparison with platinum cobalt standards with an appropriate colorimeter.

We claim:

1. A process for purifying 1,4-butanediol comprising feeding crude 1,4-butanediol into a distillation zone at the midpoint or below and at least three theoretical trays above the bottom of the zone, the distillation zone having a vacuum of less than 200 mm Hg and a temperature between 100° and 175° C., taking off an overhead stream containing water and low boilers, a bottom stream containing high boilers and a side stream containing 1,4-butanediol with a water content of less than 5000 ppm, the side stream being removed above the midpoint of the zone and at least two theoretical trays below the top of the zone, feeding side stream into the midpoint or lower of a second distillation zone having a vacuum of less than 200 mm Hg and a temperature between 100° and 175° C., taking off a bottom stream containing high boilers, an overhead stream containing water and low boilers and at a point above the feed and at least two theoretical trays from the top a product stream of 1,4-butanediol substantially free from color-forming materials to provide a product for use as a precursor in the preparation of polyesters having substantially reduced APHA color.

2. A process for removing color-forming materials from crude 1,4-butanediol by multi-stage distillation, the process consisting essentially of first bringing the water content of the crude butanediol to 5000 ppm or less by distillation at a temperature of 175° C. or less and a pressure of 200 mm of Hg or less, and then removing substantially all of the color-forming materials, to provide a product suitable for use as a precursor in the preparation of polyesters having substantially reduced APHA color.

* * * * *